United States Patent [19]

Fader et al.

[11] 3,941,564
[45] Mar. 2, 1976

[54] METHOD FOR ASSESSING THYROID FUNCTION

[75] Inventors: Marshall Lloyd Fader, South Bend; Lloyd Alan Schick, Elkhart, both of Ind.

[73] Assignee: Miles Laboratories, Inc., Elkhart, Ind.

[22] Filed: Sept. 13, 1973

[21] Appl. No.: 397,118

[52] U.S. Cl. .................... 23/230 B; 250/303; 424/1
[51] Int. Cl.[2] .................... G01N 33/16; G21H 5/02
[58] Field of Search ................ 23/230 B; 424/1, 12; 250/303

[56] References Cited
UNITED STATES PATENTS

| | | | |
|---|---|---|---|
| 3,659,104 | 4/1972 | Gross et al. | 23/230 B X |
| 3,710,117 | 1/1973 | Gross et al. | 23/230 B X |
| 3,799,740 | 3/1974 | Mincey | 23/230 B |

*Primary Examiner*—R. E. Serwin
*Assistant Examiner*—Timothy W. Hagan
*Attorney, Agent, or Firm*—Andrew L. Klawitter

[57] ABSTRACT

In vitro method for assessing thyroid function based on an indirect estimation of the free thyroxine concentration of a sample of serum. Known amounts of a sample of serum to be tested and a radioactive labeled thyroxine solution are added to an alkaline crosslinked dextran gel column which serves to dissociate the serum thyroxine bound to thyroxine binding proteins. After washing the serum proteins from the column, a portion of the mixture of labeled and serum thyroxine is eluted from the column using a known amount of the serum sample and a known amount of eluting liquid containing thyroxine binding protein. The use of a portion of the serum sample normalizes the elution of free thyroxine against the thyroxine binding capacity of the serum sample. By comparing the percent labeled thyroxine retained in the column in testing the serum sample to the percent retained in testing a reference sample representing a known thyroid condition, a free thyroxine equivalent value is obtained which is useful in differentiating hyperthyroid, euthyroid, and hypothyroid conditions. The method can be modified to provide a means for determining the total thyroxine concentration of the serum sample, as well as its free thyroxine equivalent.

31 Claims, 2 Drawing Figures

METHOD FOR ASSESSING THYROID FUNCTION

BACKGROUND OF THE INVENTION

Thyroxine (T-4) is found in serum as free thyroxine (free T-4) and as bound thyroxine (bound T-4). In its bound form, thyroxine is conjugatd with thyroxine binding proteins (TBP). The relative amount of free and bound T-4 present in serum depends on two factors; the amount of T-4 secreted by the thyroid and the concentration of TBP in the serum. The concentration of TBP may vary according to the condition of the subject. For instance, the presence of excess estrogens, such as in pregnancy and in the use of oral contraceptives, causes an increase in the TBP level. Thus, the use of of total T-4 assays for the differential determination of hyperthyroid, euthyroid and hypothyroid conditions can lead to false diagnoses. However, the percentage of free T-4 in serum varies with changes in TBP levels. Therefore, the concentration of free T-4 in serum is an indicator of thyroid function which is unchanged even during wide variances in TBP levels.

DESCRIPTION OF THE PRIOR ART

The determination of the concentration of free T-4 in serum is generally considered to be the most useful means for assessing thyroid function since free T-4 is the hormone made available to the peripheral tissues for hormonal action. The concentration of free T-4 in serum may be found by determining the percentage of free T-4 in serum and multiplying the amount of total T-4 in the serum by this percentage. While there are numerous available methods for determining the percentage of free T-4 in serum, all possess clinically disadvantageous characteristics. One frequently used method involves a prolonged dialysis of serum mixed with radioactive labeled T-4. This method, described in *J. Clin. Invest.* 44: 1679-89(1965), is time consuming and requires skills which the clinical technician generally does not have.

Recently, clinically useful methods have been found for determining total T-4 (U.S. Pat. No. 3,659,104) and a T-4 uptake index related to the number of unbound TBP sites in serum (U.S. Pat. No. 3,710,117). The arithmetic product of total T-4 and the T-4 uptake index is an indirect estimate of free T-4 which has been found to correlate with more rigorous techniques in assessing thyroid function. However, two separate tests must be conducted which multiplies the errors involved in each test and requires more time than desired.

SUMMARY OF THE INVENTION

It has now been found that a simple single test method for the indirect determination of free thyroxine in serum is provided based on the use of a second portion of the serum sample in the elution of an alkaline crosslinked dextran gel column previously contacted with radioactive labeled thyroxine and a first portion of the serum sample. The present invention is basically a modification of the total thyroxine method in U.S. Pat. No. 3,659,104. The use of a portion of the serum sample in the elution step has been found to normalize the method against the actual thyroxine binding capacity of the serum sample and therefore can be used in indirectly determining the concentration of free thyroxine in the serum sample.

The disclosed method for assessing thyroid function through the indirect determination of the free thyroxine concentration of a serum sample basically comprises the steps of (a) adding a predetermined quantity of the serum sample and a quantity of a radioactive labeled thyroxine solution to a column containing a crosslinked dextran gel at a pH of at least about 11, (b) washing the column with an aqueous alkaline solution, (c) adding a predetermined quantity of the serum sample and a predetermined quantity of an eluting liquid containing thyroxine binding protein to the column, (d) washing the column with an aqueous alkaline solution, (e) determining the ratio of radioactive labeled thyroxine retained in the column after step (d) to that added in step (a), and (f) comparing the ratio determined in step (e) to that obtained using a reference sample representing a known thyroid status in place of the serum sample in steps (a) and (c). The eluting liquid preferably includes an aqueous alkaline solution, preferably includes a buffer, and preferably has a pH of between about 7 and 10. Likewise, the aqueous alkaline solutions used in steps (b) and (d) preferably include a buffer and preferably have a pH of between about 7 and 10. A preferred eluting liquid also includes either human serum or human alpha-globulin.

The modified method for additionally determining the total thyroxine concentration of the serum sample basically comprises the steps of: (a) adding a predetermined quantity of the serum sample and a quantity of a radioactive labeled thyroxine solution to a column containing a crosslinked dextran gel at a pH of at least about 11, (b) washing the column with an aqueous alkaline solution, (c) adding a predetermined quantity of an eluting liquid containing thyroxine binding protein to the column, (d) washing the column with an aqueous alkaline solution, (e) adding a predetermined quantity of the serum sample to the column, (f) washing the column with an aqueous alkaline solution, (g) determining the ratio of radioactive labeled thyroxine retained in the column after step (d) to that added in step (a), (h) comparing the ratio determined in step (g) to ratios obtained using standard liquids containing known concentrations of thyroxine, (i) determining the ratio of radioactive labeled thyroxine retained in the column after step (f) to that added in step (a), and (j) comparing the ratio determined in step (i) to that obtained using a reference sample representing a known thyroid status in place of the serum sample in steps (a) and (e).

DESCRIPTION OF THE PREFERRED EMBODIMENTS

Figure 1:
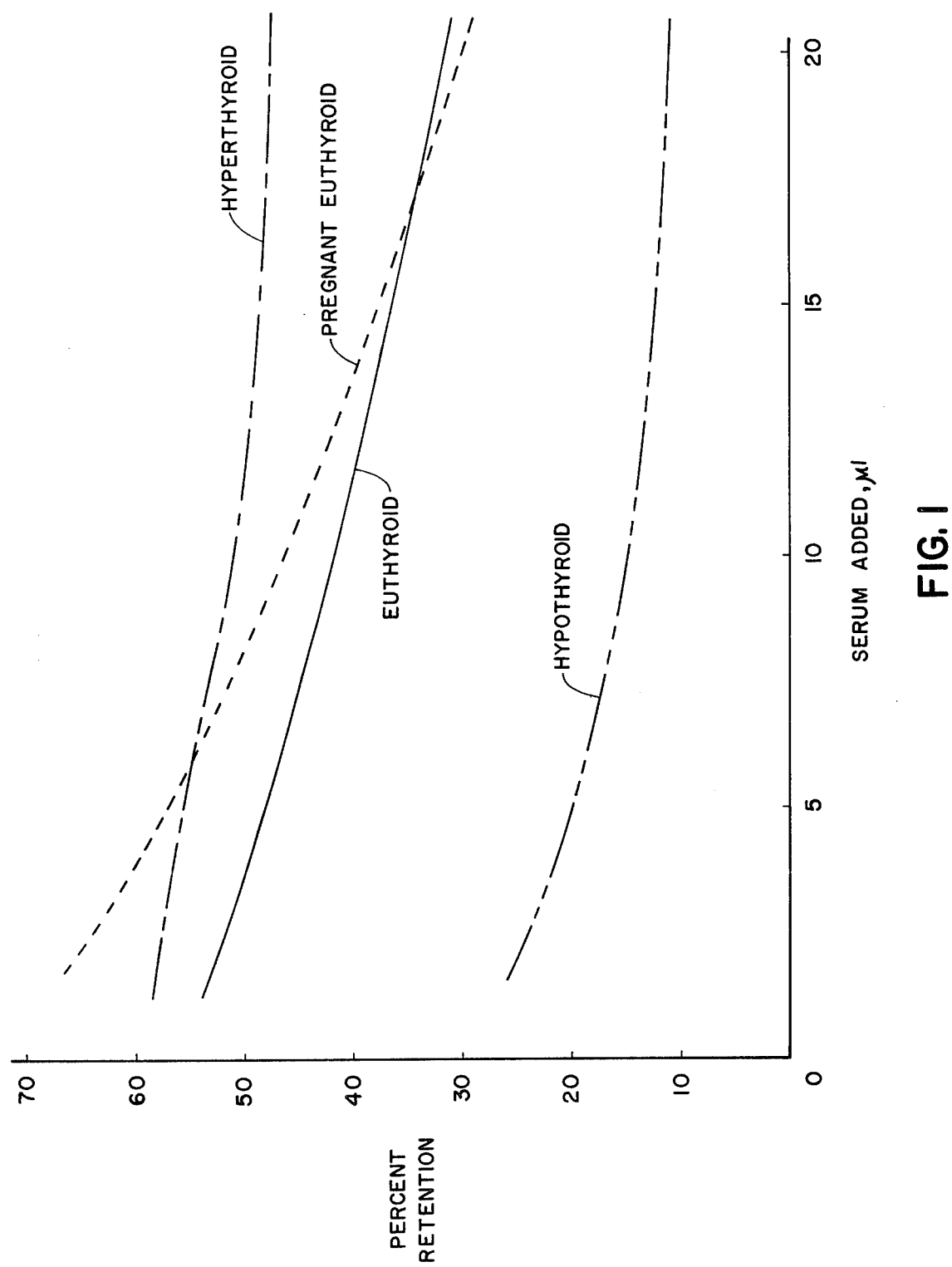
FIG. 1 is a graph showing the effect of increasing the ratio of serum to eluting liquid in the elution step with constant serum input levels for various clinical thyroid conditions.

In the methods of the present invention, a mixture of the serum sample and a radioactive labeled thyroxine solution is allowed to flow into a column which is previously equilabrated at a pH of at least 11. The strongly alkaline solution results in the dissociation of bound thyroxine to free thyroxine and its binding proteins. Thus, all of the thyroxine present in the alkaline mixture is in a free state and available for binding to the crosslinked dextran gel. The column is washed with an aqueous solution having a pH of less than 11, preferably between about 7 and 10, thereby lowering the pH of the gel environment and physically removing the serum proteins from the column. At a pH of between about 7 and 10, binding of free thyroxine to thyroxine binding protein is favored over binding to the dextran gel. Thus, the addition of the eluting liquid containing thyroxine binding protein, results in the partial removal of thyroxine from the column independent of whether the thyroxine is labeled or unlabeled (from the serum sample). By using a portion of the serum sample in this elution step, the thyroxine binding capacity of the serum sample normalizes the elution of the free thyroxine from the column. It has been found that such a normalization provides a means for assessing thyroid function based on the comparison of the proportion of labeled thyroxine retained in the column to the proportion of labeled thyroxine retained in the column when a reference sample containing a known or constant total thyroxine concentration and a known or constant thyroxine binding capacity is used in place of the serum sample following the same procedure.

As described in U.S. Pat. No. 3,659,104, alkaline crosslinked dextran gel columns can be used to determine the total thyroxine concentration of a serum sample using an eluting liquid alone, that is, not in combination with a portion of the serum sample. Therefore, the present method is easily modified to provide a means for determining total thyroxine concentration in addition to indirectly determining free thyroxine concentration by first eluting with the eluting liquid without adding a portion of the serum sample, determining the proportion of labeled thyroxine retained in the column after washing with the eluting liquid, eluting with a portion of the serum sample, and determining the proportion of labeled thyroxine retained in the column after washing with both the eluting liquid and a portion of the serum sample. The proportion of labeled thyroxine retained in the column after washing with the eluting liquid alone can then be compared to the results obtained using standards containing known total thyroxine concentrations.

Preferred dextran gels are those crosslinked with an epihalohydrin as described in U.S. Pat. No. 3,042,667 and having a water regain of from about 1 to 5 grams per gram of dry gel. Such gels are produced commercially by Pharmacia AB, Uppsala, Sweden and are sold under the tradename SEPHADEX in various ranges of molecular weight and sieve size. Of these gels, the most preferred is that which is sold under the tradename SEPHADEX G-25 which comprises dextran gel crosslinked with epichlorohydrin and which has a water regain of about 2.5 grams per gram of dry gel.

In the present methods, the aqueous alkaline solutions and the eluting liquid preferably include a buffer and preferably have a pH of between about 7 and 10. Various inorganic buffers, such as phosphate buffers, and various organic buffers, such as tris(hydroxymethyl)aminomethane, may be used. A particularly preferred buffer is a barbital buffer having a pH of about 8.6. In the modified method, for additionally determining the total thyroxine concentration, the serum sample used in the elution step is preferably mixed with an aqueous alkaline solution preferably characterized as described above.

The quantities of labeled thyroxine solution, serum sample, aqueous alkaline washing solutions, eluting liquid, and eluting serum sample may vary over a wide range. In general, specific quantities are chosen in order to provide statistically valid results. Generally, specific quantities are chosen such that the percent retention of radioactive labeled thyroxine for a serum from a mid-euthyroid subject is of the order of 50%. The relative amount of serum sample originally added to that used in the elution step affects the percent retention of radioactive labeled thyroxine. It has been found that in testing serums from subjects having different clinical conditions, the relationship between the percent retention of labeled thyroxine and the ratio between the amount of serum sample used in the eluting step and that originally added is different. FIG. 1 illustrates the relationship between percent retention and volume of eluting serum for a constant amount of eluting liquid. In the eluting step, an amount of serum sample equal to that which provides the same percent retention both for serums from female subjects having euthyroid conditions who are pregnant and from those who are not pregnant is preferably used since pregnancy is the most common condition affecting TBP levels.

It has been found that an amount of serum sample used in the eluting step which will result in the same percent retention for pregnant euthyroid subjects as for non-pregnant euthyroid subjects is an amount such that its thyroxine binding capacity is about one-half the thyroxine binding capacity of the eluting liquid. This is justified by the finding that most pregnant euthyroid sera have T-4 and TBP levels increased by about 100% over non-pregnant euthyroid sera. Thus, in testing pregnant serum the increase in thyroxine binding capacity in the eluting step due to the combination of the eluting liquid and the serum sample is inherently offset by the increase in T-4 concentration of the pregnant serum originally added to the column.

The reference sample used in the present methods represents a known thyroid condition, preferably a euthyroid condition. A preferred reference sample is a solution containing a known amount of thyroxine corresponding to a mid-euthyroid condition and no thyroxine binding capacity. The reference sample is subjected to the same procedure as the serum sample using a second column or the same column which has been thoroughly washed to remove any bound thyroxine and which has been allowed to set until any retained radioactivity has decayed to an inconsequential level. The percent retention, or ratio of radioactivity retained to that originally added of the reference sample is generally assigned an arbitrary free thyroxine equivalent (FTE) value, such as 1.0. Standard solutions from subjects whose thyroid status is known may be subjected to the same procedure and their percent retentions then compared to the reference sample results, such as in the form of a ratio, in order that ranges of free thyroxine equivalents can be assigned to hypothyroid, euthyroid, and hyperthyroid conditions.

The free thyroxine equivalent of a serum sample is calculated as follows:

$$FTE = \frac{\text{percent retention (serum sample)}}{}$$

$$\text{percent retention (reference sample)}$$

Percent retention can be determined using either a one-count or a two-count procedure. In the one-count procedure, the amount of radioactivity originally added to the column is either known or constant, whereas in the two-count procedure it is unknown. Since the amount of radioactivity originally added is constant in a one-count procedure, the FTE of the serum sample where the column is counted can be calculated as follows:

$$\text{FTE (column)} = \frac{\text{counts per time unit (serum sample)}}{\text{counts per time unit (reference sample)}}$$

Using the two-count procedure, since the amount of radioactivity originally added is unknown, the percent retentions must first be calculated as follows for both the serum and the reference samples:

$$\text{percent retention} = \frac{\text{final counts per time unit} \times 100}{\text{initial counts per time unit}}$$

In the one-count procedure, the eluate may be counted rather than the column in which case the FTE value is inverted. Thus the FTE is calculated as follows:

$$\text{FTE (eluate)} = \frac{\text{counts per time unit (reference sample)}}{\text{counts per time unit (serum sample)}}$$

The present invention will now be illustrated, but is not intended to be limited by the following Examples.

EXAMPLE 1

This example relates to the preparation of the column which is preferably used in the present method.

Five hundred (500) grams of dry SEPHADEX G-25 gel, available from Pharmacia AB, Uppsala, Sweden, was suspended in two liters of distilled water and allowed to hydrate overnight. Fines were removed by slurrying the gel in 0.1N sodium hydroxide for about 5 minutes, allowing the gel to settle for 15 minutes, and drawing off the supernatant by suction. This process was repeated three times and the gel was then suspended in 4.4 liters of 0.1N sodium hydroxide. Four (4) ml of this suspension was placed in a 6 ml plastic syringe barrel having a diameter of 13 mm and a length of 66 mm. The barrel was prefitted with a bottom closure means, such as a removable cap, and a detergent treated sintered polyethylene retaining disk about 1.5 mm thick having a diameter of 13 mm was previously pressed coaxially to the bottom of the plastic barrel. After the suspension was placed in the barrel, the suspension was stirred and allowed to settle free of air bubbles. A second detergent treated sintered polyethylene retaining disk was then inserted into the syringe barrel and pressed coaxially into firm contact with the gel such that about 1.5 ml of sodium hydroxide solution remained above the upper disk. The upper end of the syringe was then closed with a polyethylene cap. This procedure provides a column containing about 450 mg of gel.

EXAMPLE 2

This example describes a procedure for determining the FTE of a serum sample using a one-count procedure wherein either the column radioactivity or the eluate radioactivity is measured.

1. A column is prepared as in Example 1, its top cap is removed and the supernatant NaOH is discarded.

2. With the column in an upright position, 0.5 ml of $^{125}$I-labeled T-4 in 0.1N NaOH (containing a known or constant radioactivity, generally about 50,000 cpm/0.5 ml) and 0.3 ml of the serum sample to be tested are added to the column. The column is gently swirled to mix the serum and the labeled T-4. The bottom cap is removed and the serum labeled T-4 mixture is allowed to flow into the column.

3. When drainage ceases, 4.0 ml of 0.075 M barbital buffer (pH 8.6) is added to the column.

4. When drainage ceases, the column tip is blotted, the bottom cap is replaced, and 0.5 ml of 3.75 mg/ml human alpha-globulin in 0.075 M barbital buffer (pH 8.5) and 20 $\mu$l of the serum sample are added to the column. The column is gently swirled to mix the eluting liquid and the serum.

5. The bottom cap is removed and the column is allowed to drain. If the eluate radioactivity is to be measured, the drainage is collected in a radioactivity counting tube.

6. When drainage ceases, 4.0 ml of 0.075 M barbital buffer (pH 8.6) is added to the column and the column is allowed to drain. If the eluate radioactivity is to be measured the drainage is collected in the same counting tube as that used in step 5.

7. If the column radioactivity is to be measured, the bottom cap is replaced, the column is placed in a gamma counter, and the counts per minute recorded as cpm (serum sample). If the eluate radioactivity is to be measured, the counting tube used in steps 5 and 6 is placed in a gamma counter and the counts per minute recorded as cpm (serum sample).

8. Steps 1-7 are repeated using a reference sample in place of the serum sample in steps 2 and 4. The reference sample consists of human serum in 0.1N NaOH containing 2.0 mg/100ml T-4 I.

Where the column radioactivity is measured, the FTE is calculated as follows:

$$\text{FTE (one-count, column)} = \frac{\text{cpm (serum sample)}}{\text{cpm (reference solution)}}$$

where the eluate radioactivity is measured, the FTE is calculated as follows:

$$\text{FTE (one-count, eluate)} = \frac{\text{cpm (reference solution)}}{\text{cpm (serum sample)}}$$

EXAMPLE 3

This example describes a procedure for determining the FTE of a serum sample using a two-count procedure wherein the column radioactivity is measured.

The procedure is the same as that described in Example 2 where the column radioactivity is measured with the following exceptions: the 0.5 ml volume of $^{125}$I-labeled T-4 in 0.1N NaOH contains an unknown or variable radioactivity, generally between 60,000 and 120,000 cpm/0.5 ml; between steps 3 and 4, the bottom cap is replaced, the column is placed in a gamma counter, the counts per minute are recorded as initial cpm, and the bottom cap is removed; the counts per minute measured in step 7 are recorded as final cpm; and the FTE is calculated as follows:

$$\text{FTE (two-count)} = \frac{\text{\% retention (serum sample)}}{\text{\% retention (reference solution)}}$$

where $$\text{\% retention} = \frac{\text{final cpm} \times 100}{\text{initial cpm}}$$

EXAMPLE 4

This example describes a procedure for determining both the FTE and the T-4 I concentration of a serum sample using a single column scheme.

Each of the procedures described in Examples 2 and 3 can be modified to provide both the FTE and the T-4 I concentration of a serum sample by following the procedures described in those examples with the following additions and exceptions:

A. In step 4, 1.0 ml of the human alpha-globulin liquid is added to the column (rather than 0.5 ml) and no serum (or reference solution) is added.

B. Between steps 4 and 5, the following steps are performed: the bottom cap is removed and the column is allowed to drain (if the eluate radioactivity is to be measured, the drainage is collected in a radioactivity counting tube); when drainage ceases, 4.0 ml of 0.075 M barbital buffer (pH 8.6) is added to the column and the column is allowed to drain (if the eluate radioactivity is to be measured, the drainage is collected in the same counting tube); if the column radioactivity is to be measured, the bottom cap is replaced, the column is placed in a gamma counter, and the counts per minute are recorded as cpm (T-4 I) (if the eluate radioactivity is to be measured the collecting tube is placed in the gamma counter and the counts per minute recorded); and 0.5 ml of 0.075 M barbital buffer (pH 8.6) and 20 μl of the serum sample (or reference sample) are added to the column and the column is gently swirled to mix the buffer and the serum (or reference sample).

C. The T-4 I concentration is determined by comparing the percent retention (T-4 I) to a standard curve where, using a one-count procedure and measuring the eluate radioactivity in step B above, $$\text{\% retention (T-4 I, eluate)} = 100 - \frac{\text{cpm (T-4 I)} \times 100}{\text{known cpm added}}$$

where, using a one-count procedure and measuring the column radioactivity in step B above $$\text{\% retention (T-4 I, column)} + \frac{\text{cpm (T-4 I)} \times 100}{\text{known cpm added originally}}$$

and where, using a two-count procedure and measuring the column radioactivity in step B above, $$\text{\% retention (T-4 I, column)} = \frac{\text{cpm (T-4 I)} \times 100}{\text{initial cpm}}$$

In these procedures for determining both the FTE and the T-4 I concentration of the serum sample, once a one-count or a two-count procedure is chosen, that procedure is followed for both the FTE and the T-4 I concentration determinations; however, the choice of whether the column radioactivity or the eluate radioactivity is to be measured is independent of whether the FTE or the T-4 I concentration is being determined. For instance, using a one-count procedure, % retention (T-4 I) can be determined by measuring the eluate radioactivity and the FTE can be determined by measuring the column radioactivity and vice versa.

EXAMPLE 5

This example relates to the determination of the FTE of samples having known thyroid statuses and the correlation between the FTE's of the samples determined using the procedure described in Example 2 and the FTI values obtained following the procedures described in U.S. Pat. Nos. 3,659,104 and 3,710,117.

Figure 2:
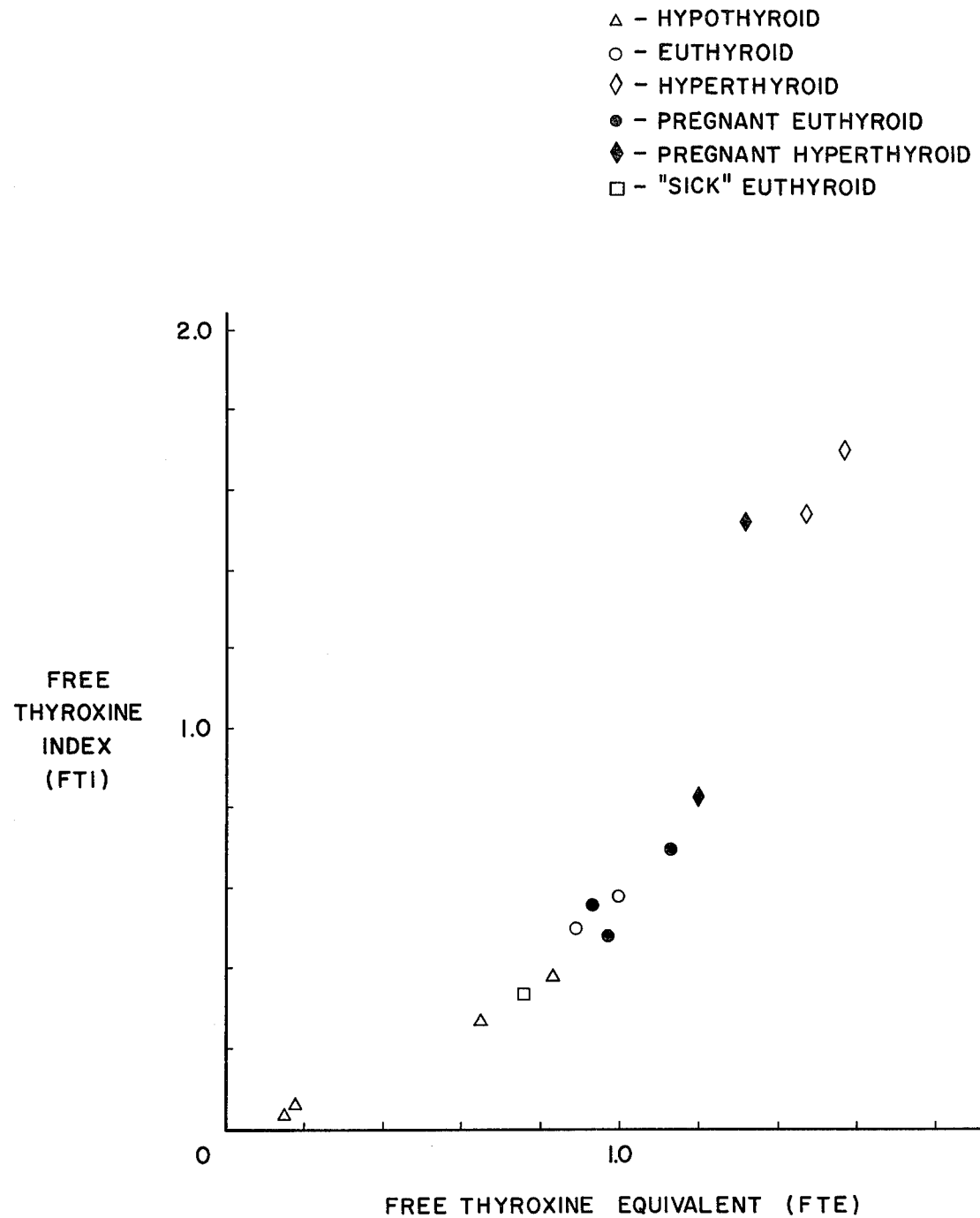
FIG. 2 is a graph showing the correlation between the free thyroxine equivalent (FTE) calculated using the present method and the free thyroxine index (FTI) calculated based on the two test procedures described in U.S. Pat. Nos. 3,659,104 and 3,710,117 and the correlation between these indices and the clinical thyroid condition of the subject.

Fourteen (14) serum samples representing different thyroid status were tested according to the procedure described in Example 2 yielding the FTE of each sample. The FTI values were calculated as follows:

$$\text{FTI} = \text{T-4 I concentration} \times \frac{\text{T-3 uptake value}}{\text{mean T-3 uptake value in euthyroid subjects}}$$

where T-4 I concentration and the T-3 uptake value were obtained following the procedures described in U.S. Pat. No. 3,659,104 and Example 1 of U.S. Pat. No. 3,710,117 respectively. The results yielded the graph shown in FIG. 2 of the drawings.

What is claimed is:

1. A method for assessing thyroid function through the indirect determination of the free thyroxine concentration of a serum sample comprising the steps of:
   a. adding to a column containing a crosslinked dextran gel at a pH of at least about 11 a first predetermined quantity of said serum sample and a quantity of a radioactive labeled thyroxine solution, whereby substantially all of the thyroxine from said first serum sample quantity becomes dissociated from endogenous thyroxine binding protein and at least a portion of both the resulting dissociated thyroxine and the radioactive labeled thyroxine from said quantity of radioactive thyroxine solution becomes bound to said crosslinked dextran gel,
   b. washing said column with an aqueous alkaline solution having a pH of less than 11, whereby substantially all of the thyroxine binding protein from said first serum sample quantity is removed from said column, the pH of the crosslinked dextran gel environment is reduced to less than 11, and all of the thyroxine from said first serum sample quantity and all of the radioactive labeled thyroxine remaining in contact with said gel is bound to said gel,
   c. adding to said column a second predetermined quantity of said serum sample and a predetermined quantity of an eluting liquid containing thyroxine binding protein, whereby at least a portion of the thyroxine from said first serum sample quantity and of the radioactive labeled thyroxine bound to said gel after step (b) is dissociated therefrom and becomes bound to thyroxine binding protein from said eluting liquid or said second serum sample quantity, d. washing said column with an aqueous alkaline solution having a pH of less than 11, whereby the thyroxine from said first serum sample quantity and the radioactive labeled thyroxine which became bound to thyroxine binding protein in step (c) are sustantially completely removed from said column, e. determining the ratio of radioactive labeled thyroxine retained in said column after step (d) to that added in step (a), and f. comparing the ratio determined in step (e) to that obtained using a reference sample representing a known thyroid status in place of said serum sample in steps (a) and (c).

2. A method as in claim 1 wherein said quantity of radioactive labeled thyroxine solution contains a predetermined amount of radioactivity and wherein steps (e) and (f) are accomplished by determining the ratio between the radioactivity retained in said column after step (d) to that retained using said reference solution.

3. A method as in claim 1 wherein said quantity of radioactive labeled thyroxine solution contains an unknown amount of radioactivity and wherein step (e) is accomplished by comparing the radioactivity retained in said column after step (b) to that retained in said column after step (d).

4. A method as in claim 1 wherein said eluting liquid includes an aqueous alkaline solution.

5. A method as in claim 4 wherein said aqueous alkaline solution has a pH of between about 7 and 10.

6. A method as in claim 4 wherein said aqueous alkaline solution includes a buffer.

7. A method as in claim 6 wherein said buffer is a barbital buffer having a pH of about 8.6.

8. A method as in claim 1 wherein the amount of said serum sample added to said column in step (c) is such that its thyroxine binding capacity is about one-half the thyroxine binding capacity of the eluting liquid.

9. A method as in claim 1 wherein said aqueous solutions in steps (b) and (d) have a pH of between about 7 and 10.

10. A method as in claim 1 wherein said aqueous solutions in steps (b) and (d) include a buffer.

11. A method as in claim 10 wherein said buffer is a barbital buffer having a pH of about 8.6.

12. A method as in claim 1 wherein said dextran gel is crosslinked with an epihalohydrin and has a water regain of from about 1 to 5 grams per gram of dry gel.

13. A method as in claim 1 wherein said eluting liquid includes human alpha-globulin.

14. A method as in claim 1 wherein said eluting liquid includes human serum.

15. A method for both determining the total thyroxine concentration of a serum sample and assessing thyroid function through the indirect determination of the free thyroxine concentration of said serum sample comprising the steps of:

a. adding to a column containing a crosslinked dextran gel at a pH of at least about 11 a first predetermined quantity of said serum sample and a quantity of a radioactive labeled thyroxine solution, whereby substantially all of the thyroxine from said first serum sample quantity becomes dissociated from endogenous thyroxine binding protein and at least a portion of both the resulting dissociated thyroxine and the radioactive labeled thyroxine from said quantity of radioactive thyroxine solution becomes bound to said crosslinked dextran gel, b. washing said column with an aqueous alkaline solution having a pH of less than 11, whereby substantially all of the thyroxine binding protein from said first serum sample quantity is removed from said column, the pH of the crosslinked dextran gel environment is reduced to less than 11, and all of the thyroxine from said first serum sample quantity and all of the radioactive labeled thyroxine remaining in contact with said gel is bound to said gel, c. adding to said column a predetermined quantity of an eluting liquid containing thyroxine binding protein, whereby at least a portion of the thyroxine from said first serum sample quantity and of the radioactive labeled thyroxine bound to said gel after step (b) is dissociated therefrom and becomes bound to thyroxine binding protein from said eluting liquid, d. washing said column with an aqueous alkaline solution having a pH of less than 11, whereby the thyroxine from said first serum sample quantity and the radioactive labeled thyroxine which became bound to thyroxine binding protein in step (c) are substantially completely removed from said column, e. adding to said column a second predetermined quantity of said serum sample, whereby the presence in said second serum sample quantity of unsaturated thyroxine binding protein causes at least a portion of the radioactive labeled thyroxine bound to said gel after step (d) to dissociate therefrom and become bound to thyroxine binding protein from said second serum sample quantity, f. determining the amount of radioactivity retained in said column after step (d) or (e), g. washing said column with an aqueous alkaline solution having a pH of less than 11, whereby the thyroxine from said first serum sample quantity and the radioactive labeled thyroxine which became bound to thyroxine binding protein in step (e) are substantially completely removed from said column, h. determining the ratio of radioactive labeled thyroxine retained in said column after step (d) or (e) to that added in step (a), i. comparing the ratio determined in step (h) to ratios obtained using standard liquids containing known concentrations of thyroxine, j. determining the ratio of radioactive labeled thyroxine retained in said column after step (g) to that added in step (a), and k. comparing the ratio determined in step (j) to that obtained using a reference sample representing a known thyroid status in place of said serum sample in steps (a) and (e).

16. A method as in claim 15 wherein said quantity of radioactive labeled thyroxine solution contains a predetermined amount of radioactivity and wherein steps (j) and (k) are accomplished by determining the ratio between the radioactivity retained in said column after step (g) to that retained using said reference solution.

17. A method as in claim 15 wherein said quantity of radioactive labeled thyroxine solution contains an unknown amount of radioactivity and wherein step (j) is accomplished by comparing the radioactivity retained in said column after step (b) to that retained in said column after step (f).

18. A method as in claim 15 wherein said eluting liquid includes an aqueous alkaline solution.

19. A method as in claim 18 wherein said aqueous alkaline solution has a pH of between about 7 and 10.

20. A method as in claim 18 wherein said aqueous alkaline solution includes a buffer.

21. A method as in claim 20 wherein said buffer is a barbital buffer having a pH of about 8.6.

22. A method as in claim 15 wherein an aqueous alkaline solution is also added to said column in step (e).

23. A method as in claim 22 wherein said aqueous alkaline solution has a pH of between about 7 and 10.

24. A method as in claim 22 wherein said aqueous alkaline solution includes a buffer.

25. A method as in claim 24 wherein said buffer is a barbital buffer having a pH of about 8.6.

26. A method as in claim 15 wherein said dextran gel is crosslinked with an epihalohydrin and has a water regain of from about 1 to 5 grams per gram of dry gel.

27. A method as in claim 15 wherein said eluting liquid includes human alpha-globulin.

28. A method as in claim 15 wherein said eluting liquid includes human serum.

29. A method as in claim 15 wherein said aqueous solutions in steps (b), (d), and (g) have a pH of between about 7 and 10.

30. A method as in claim 15 wherein said aqueous solutions in steps (b), (d), and (g) include a buffer.

31. A method as in claim 30 wherein said buffer is a barbital buffer having a pH of about 8.6.

* * * * *